(12) United States Patent
Jackson et al.

(10) Patent No.: US 10,475,216 B2
(45) Date of Patent: Nov. 12, 2019

(54) IMAGING SYSTEM AND METHOD USING LEARNED PHASE ACQUISITION TO ACQUIRE IMAGES

(71) Applicant: General Electric Company, Schenectady, NY (US)

(72) Inventors: John Irvin Jackson, Brookfield, WI (US); John Londt, Oconomowoc, WI (US); Eric Gros, Waukesha, WI (US); Dave Chevalier, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 81 days.

(21) Appl. No.: 15/905,351

(22) Filed: Feb. 26, 2018

(65) Prior Publication Data

US 2019/0266760 A1    Aug. 29, 2019

(51) Int. Cl.
*G06K 9/00* (2006.01)
*G06T 11/00* (2006.01)
(Continued)

(52) U.S. Cl.
CPC ........ *G06T 11/005* (2013.01); *A61B 5/02405* (2013.01); *A61B 6/032* (2013.01); *A61B 6/486* (2013.01); *A61B 6/503* (2013.01); *G06T 7/0016* (2013.01); *G06T 7/20* (2013.01); *A61B 6/025* (2013.01); *G06T 2207/10081* (2013.01); *G06T 2207/20076* (2013.01); *G06T 2207/30048* (2013.01)

(58) Field of Classification Search
CPC .......................................... G06T 2207/30048
See application file for complete search history.

(56) References Cited

U.S. PATENT DOCUMENTS 6,353,653 B1    3/2002    Edic
6,628,743 B1    9/2003    Drummond et al.
(Continued)

OTHER PUBLICATIONS

Cho et al., "Motion-compensated Image Reconstruction for Cardiac CT with Sinogram-Based Motion Estimation", 978-1-4799-0534-8/13/, 2013, IEEE, 978-1-4799-0534-8/13/, (5 pages).
(Continued)

*Primary Examiner* — Oneal R Mistry
(74) *Attorney, Agent, or Firm* — Dean D. Small; The Small Patent Law Group, LLC

(57) ABSTRACT

An imaging system determines a heart rate of a patient, a cardiac disease state, and/or a target cardiac anatomy of the patient. The system calculates an image acquisition time range from a patient population model using the heart rate, the cardiac disease state, and/or the target anatomy. The model represents relationships between cardiac motion of other patients and time or cardiac phases of the other patients. The system also determines imaging settings to acquire image data of the target anatomy during the image acquisition time range that is calculated. Imaging the target anatomy of the patient according to the imaging settings generates image data of the target anatomy having less cardiac motion and/or a reduced image acquisition time range relative to determining the imaging settings without using the patient population model.

20 Claims, 7 Drawing Sheets

(51) Int. Cl.
*A61B 6/03* (2006.01)
*A61B 6/00* (2006.01)
*A61B 5/024* (2006.01)
*G06T 7/20* (2017.01)
*G06T 7/00* (2017.01)
*A61B 6/02* (2006.01)

(56) References Cited

U.S. PATENT DOCUMENTS

| | | | |
|---|---|---|---|
| 6,721,386 B2 | 4/2004 | Bulkes et al. | |
| 8,811,707 B2 | 8/2014 | Jackson et al. | |
| 8,917,925 B1 | 12/2014 | Grady et al. | |
| 9,208,747 B2 | 12/2015 | Guehring et al. | |
| 9,629,587 B2 | 4/2017 | Okerlund et al. | |
| 9,662,017 B2 | 5/2017 | Giri et al. | |
| 2010/0272322 A1* | 10/2010 | Koehler | A61B 6/032 382/107 |
| 2011/0164800 A1* | 7/2011 | Kokubun | A61B 6/032 382/131 |
| 2012/0294427 A1* | 11/2012 | Grady | A61B 6/481 378/95 |
| 2013/0294667 A1 | 11/2013 | Zheng et al. | |
| 2014/0022250 A1 | 1/2014 | Mansi et al. | |
| 2015/0265234 A1 | 9/2015 | Kyriakou | |
| 2015/0285884 A1 | 10/2015 | Giri et al. | |
| 2017/0209113 A1 | 7/2017 | Jackson et al. | |

OTHER PUBLICATIONS

Wang et al., "Clinical Evaluation of New Automatic Coronary-specific Best Cardiac Phase Selection Algorithm for Single-beat Coronary CT Angiography", Research Article, Feb. 23, 2017, PLoS One, DOI:10.1371/journal.pone.0172686 (11 pages).

* cited by examiner

IMAGING SYSTEM AND METHOD USING LEARNED PHASE ACQUISITION TO ACQUIRE IMAGES

FIELD

The subject matter disclosed herein relates generally to imaging systems, and more particularly to non-invasive imaging systems.

BACKGROUND

Non-invasive imaging technologies allow images of the internal structures of a patient or object to be obtained without performing an invasive procedure on the patient or object. Technologies such as computed tomography (CT) use various physical principals, such as the differential transmission of x-rays through the target volume, to acquire image data and to construct tomographic images (e.g., three-dimensional representations of the interior of the human body or of other imaged structures).

Imaging moving bodies, such as the heart, presents problems in terms of obtaining clear images of the bodies during movement. Currently, the periodic movement of a heart is accounted for in cardiac imaging by predicting when the cardiac motion will be the smallest and then acquiring data during a range larger than the minimum duration required, to allow for errors in the prediction of the time interval with least motion, and to allow for deviations from strictly periodic motion. Images can be reconstructed from multiple times intervals within the data acquisition window. Image slices or volumes generated from data acquired during these different phases will show different amounts of motion. To obtain a clear image of the heart when the movement of the heart is reduced or temporarily eliminated, the many image slices may be acquired over a significant portion of a cardiac cycle.

For example, the heart rate of a patient can be determined. A significant portion of the cardiac cycle (e.g., from 35% to 85% of the R-R interval) can be used for a data acquisition window. The heart is exposed to x-rays during this time. This significant portion of the cardiac cycle can result in significant exposure of the heart and surrounding tissue to potentially damaging x-rays. Additionally, if the patient has an irregular heart rate, this acquisition window can be increased, which also results in significant exposure of the heart and surrounding tissue to potentially damaging x-rays.

A need exists to improve imaging of moving bodies, such as hearts, to obtain clear images of the moving bodies while movement of the bodies is reduced or eliminated, while also reducing exposure of the patient to x-rays used to acquire the images.

BRIEF DESCRIPTION

In one embodiment, an imaging system includes one or more processors configured to determine one or more of a heart rate of a patient under examination, a cardiac disease state of the patient under examination, and/or an imaging target portion of cardiac anatomy of the patient under examination. The one or more processors also are configured to calculate an image acquisition time range from a patient population model using the one or more of the heart rate, the cardiac disease state, and/or the imaging target portion of the cardiac anatomy. The patient population model represents relationships between cardiac motion of plural other patients and one or more of time or cardiac phases of the other patients.

The one or more processors also are configured to determine imaging configuration settings for an imaging assembly to acquire image data of the target cardiac anatomy of the patient under examination during the image acquisition time range that is calculated using the patient population model. Imaging the target cardiac anatomy of the patient under examination using the imaging assembly operating according to the imaging configuration settings generates image data of the target cardiac anatomy having less cardiac motion and/or a reduced image acquisition time range relative to determining the imaging configuration settings without using the patient population model.

The one or more processors are configured to generate and communicate a control signal that directs the imaging assembly to image the target cardiac anatomy of the patient under examination using the imaging configuration settings. The one or more processors also are configured to receive imaging data from the imaging assembly, to reconstruct one or more images of the target cardiac anatomy using the imaging data, and to one or more of direct display of the one or more images on an electronic display device or direct storage of the one or more images in a tangible and non-transitory computer readable storage medium.

In one embodiment, a method includes determining one or more of a heart rate of a patient under examination, a cardiac disease state of the patient under examination, and/or an imaging target portion of cardiac anatomy of the patient under examination. The method also includes calculating an image acquisition time range from a patient population model using the one or more of the heart rate, the cardiac disease state, and/or the imaging target portion of the cardiac anatomy. The patient population model represents relationships between cardiac motion of plural other patients and one or more of time or cardiac phases of the other patients. The method also includes determining imaging configuration settings for an imaging system to acquire image data of the target cardiac anatomy of the patient under examination during the image acquisition time range that is calculated using the patient population model. Imaging the target cardiac anatomy of the patient under examination using the imaging configuration settings for the imaging system generates image data of the target cardiac anatomy having less cardiac motion and/or a reduced image acquisition time range relative to determining the imaging configuration settings without using the patient population model.

In one embodiment, a tangible and non-transitory computer readable storage medium is provided that includes instructions that direct one or more processors to determine one or more of a heart rate of a patient under examination, a cardiac disease state of the patient under examination, and/or an imaging target portion of cardiac anatomy of the patient under examination. The instructions also direct the one or more processors to calculate an image acquisition time range from a patient population model using the one or more of the heart rate, the cardiac disease state, and/or the imaging target portion of the cardiac anatomy. The patient population model represents relationships between cardiac motion of plural other patients and one or more of time or cardiac phases of the other patients. The instructions also direct the one or more processors to determine imaging configuration settings for an imaging system to acquire image data of the target cardiac anatomy of the patient under examination during the image acquisition time range that is calculated using the patient population model. Imaging the target cardiac anatomy of the patient under examination using the imaging configuration settings for the imaging system generates image data of the target cardiac anatomy having less cardiac motion and/or a reduced image acquisition time range relative to determining the imaging configuration settings without using the patient population model.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
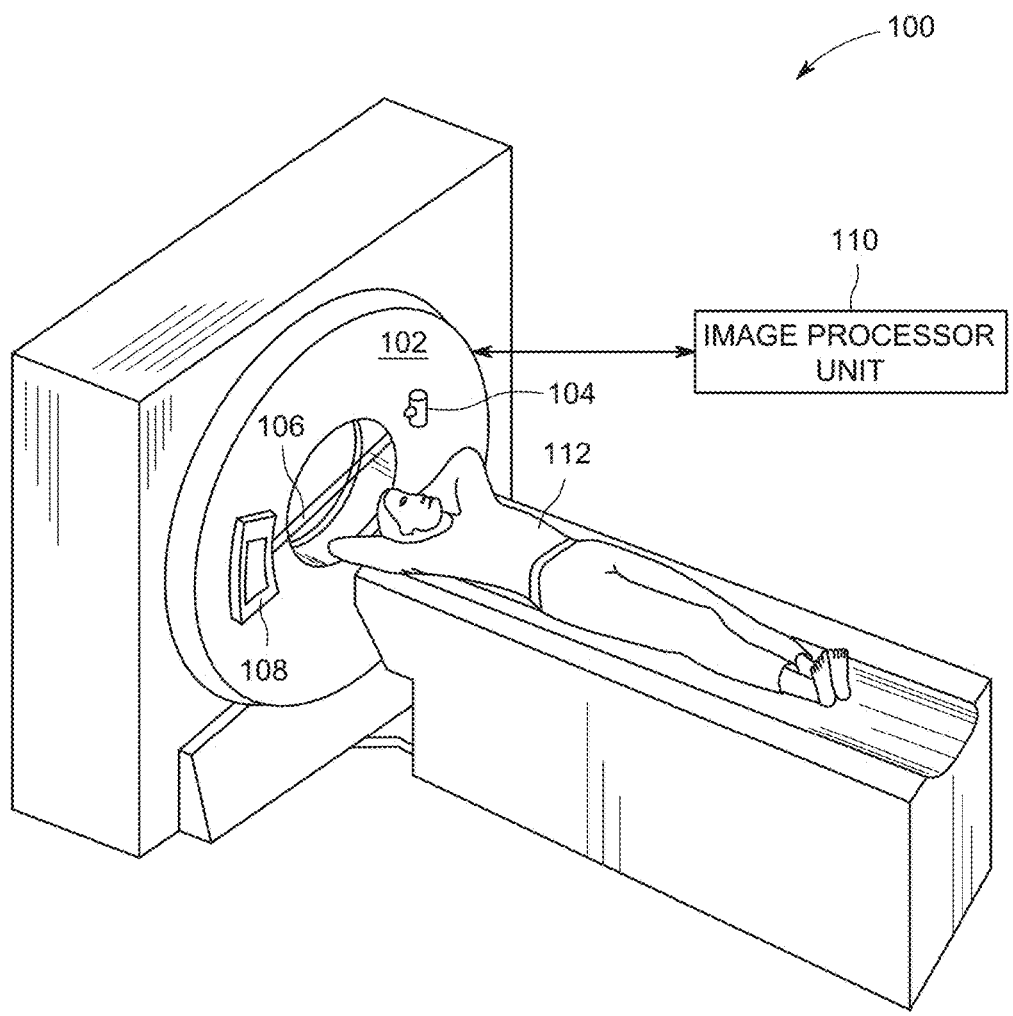
FIG. 1 illustrates one embodiment of an imaging system.

One or more embodiments of the inventive subject matter described herein provide for imaging systems and methods that obtain images of moving bodies (e.g., hearts) with less exposure of the patient to electromagnetic imaging waves (e.g., x-rays), while avoiding a reduction in image quality or even improving upon the image quality relative to known systems and techniques. The systems and methods can identify smaller or different image acquisition windows within the R-R intervals of hearts than current systems and methods, thereby reducing exposure of patients to x-rays.

The systems and methods can obtain measurements of movements of target cardiac anatomy derived from sets of image data acquired from different patients and can generate a database of cardiac motion versus time or phase. The measurements of movements can be obtained from a patient population having a variety of patients with different cardiac disease states (e.g., the presence or absence of cardiac disease, and optionally the type or identity of cardiac disease), different ages, different heart rates, different genders, and the like. The disease state can be any of a variety of cardiac diseases, such as mitral stenosis, heart failure, left ventricular dyssynchrony, cardiac output, and/or stroke volume.

The measurements of movements can be used to create the motion versus time database that represents how hearts of patients of different cardiac disease states, ages, genders, heart rates, etc., move or are likely to move. This database can be used by the systems and methods to statistically recommend or select the time or phase range during which the target cardiac anatomy of a patient should be exposed to x-rays during a cardiac exam.

The database represents historical patient cardiac data of other patients and, optionally, a patient that is about to be imaged (referred to as the patient-under-examination). Using this historical data, the systems and methods can predict or estimate an image acquisition time or phase of reduced or least cardiac motion based on a variety of factors, such as the heart rate of the patient-under-examination, the heart rhythm of the patient-under-examination (as well as any rhythm abnormalities that result in the heart rate of the patient changing over time, such as bigeminy), or other a priori conditions (such as cardiac disease, for example dyssynchrony or valvular disease). One or more acquisition times or phases can be determined from this database based on some or all of these factors.

For example, a set of historical patient data in the database associated with one or more patients having the same or similar factors can be examined to identify which portion or portions of an R-R interval of the target cardiac anatomy of the patient-under-examination is likely or most likely to have less motion than larger or smaller portions of the R-R interval. This set of historical data can be imaging data and data indicative of the same factors of other patients (and, potentially of the patient-under-examination). The factors of the patient-under-examination can be compared with the factors of the patients represented in the database to identify the set of historical data, such as by finding previously imaged patients having the same or similar cardiac disease or absence of cardiac disease, the same or similar progression or severity of cardiac disease, the same or similar age, the same or similar heart rates or heart rate patterns, and/or the same gender as the patient-under-examination. The factors may be similar when the value of the factor of the patient-under-examination is within a designated range of the value of the corresponding factor of another patient, such as heart rates within 10% of each other, ages within 5% of each other, etc.

The patient-under-examination can then be imaged (e.g., exposed to x-rays) over the same portion of the R-R interval as the R-R interval identified in the database as having reduced or no motion of the heart (relative to another portion of the R-R interval). Alternatively, instead of the systems and methods attempting to identify and acquire image data over the phase or time with the least amount of motion in the target cardiac anatomy, the systems and methods can identify and acquire image data over the phase or time having motion that can be removed with motion correction techniques.

By identifying the portion of the R-R interval having reduced cardiac motion in the target anatomy (or having motion that can be more easily removed with motion correction techniques), the acquisition range (e.g., time period) may be reduced. This can be a significantly safer approach then merely using the same, default portion of the R-R interval for imaging, as is known to be done today. For example, the amount or energy of the x-rays to which the chest and surrounding tissue of the patient-under-examination is exposed during imaging can be reduced, while still obtaining clear images of the target cardiac anatomy. Reducing the energy to which the patient-under-examination is exposed gives a corresponding reduction in the likelihood of radiation-induced health problems to the affected tissue of patients, which is especially important for female patients (by reducing exposure of female breast tissue to the x-rays) and young patients having cardiac diseases (who are more likely to require repeated cardiac imaging sessions over a longer portion of their lives relative to older patients or patients without cardiac disease).

The database of historical patient data can reveal different portions of the R-R interval for cardiac imaging for a patient-under-examination based on which region of the heart is being imaged. For example, the proximal or distal locations of each coronary and/or different cardiac valves may have different expected motions during different portions of the R-R interval based on the historical patient data (the left circumflex artery, the left anterior descending artery, and the right coronary artery may be expected to move different amounts at different times during a cardiac cycle based on the database).

Optionally, the systems and methods can determine a dose (e.g., cost) versus confidence metric for the acquisition phase of the R-R interval that is obtained from the database. The dose versus confidence metric can indicate a percentage or other measurement of how likely imaging during the corresponding phase of the R-R interval is to obtain images of the target cardiac anatomy with little to no motion (relative to another portion of the R-R interval). Some larger phases or portions of the R-R interval may have large confidence metrics, but these metrics also are associated with increased exposure of the patient-under-examination to x-rays. In some situations, a smaller phase or portion of the R-R interval may have a slightly smaller confidence metric (e.g., 1-2% smaller), but a significantly reduced amount of exposure of the patient-under-examination to x-rays. The systems and methods can balance how likely it is that the imaging apparatus will acquire images of the target cardiac anatomy with reduced or no motion against the exposure of x-rays to the patient. For different phases of the R-R interval having different confidence metrics, the systems and methods can select a slightly smaller (e.g., less than 5% smaller) confidence metric if the corresponding phase of the R-R interval results in the patient-under-examination being exposed to a smaller dose of x-rays.

The target cardiac anatomy of the patient-under-examination can then be imaged over or during the selected phase or phases of the R-R interval of the patient-under-examination, and the acquired imaging data can be examined by the systems and methods. After the image data is at least partially acquired, use the database to determine which phase or phases to reconstruct, and whether or not to force additional motion correction processing, avoid motion correction processing, or conditionally use motion correction processing based on automated analysis (e.g., an auto phase algorithm) or user input.

At least one technical effect of the inventive subject matter described herein is to determine a shorter time interval over which to transmit x-rays into a target cardiac anatomy of a patient (and, optionally, to transmit the x-rays) while there is reduced motion of the target cardiac anatomy. This allows for clearer images to be obtained (due to the reduced motion) while also reducing the exposure of the patient to x-rays.

The image data optionally can be analyzed using reconstruction techniques (such as SmartPhase from GE Healthcare) or a post-reconstruction technique (such as SnapShot Freeze from GE Healthcare) to generate and save some measurement of cardiac motion versus phase of the target cardiac anatomy. Optionally, other measurements of motion of the target cardiac anatomy versus time may be used. For example, if the systems and methods are used to reconstruct images of multiple phases of the target cardiac anatomy, then a motion estimator or corrector (e.g., SnapShot Freeze, or SSF) could be used in connection with those images and the results saved. Additionally, when multiple phases are reconstructed, the phase sent for further processing may be inferred as the best phase for that patient.

Reconstructing an image is not intended to exclude embodiments of the inventive subject matter in which data representing an image is generated, but a viewable image is not. Therefore, an image can refer to both viewable images and data representing a viewable image. Many embodiments of the inventive subject matter generate (or are configured to generate) at least one viewable image.

Although a computed tomography (CT) system is described by way of example, the inventive subject matter also may be used to acquire images using other imaging modalities, such as tomosynthesis, MM, C-arm angiography, and so forth. The present discussion of a CT imaging modality is provided as one example of one suitable imaging modality.

Various embodiments may be implemented in connection with different types of imaging systems. For example, various embodiments may be implemented in connection with a CT imaging system or apparatus in which an x-ray source projects a fan- or cone-shaped beam that is collimated to lie within an x-y plane of a Cartesian coordinate system and generally referred to as an imaging plane. The x-ray beam passes through an object being imaged, such as a target cardiac anatomy of a patient. The beam, after being attenuated by the object, impinges upon an array of radiation detectors. The intensity of the attenuated radiation beam received at the detector array is dependent upon the attenuation of an x-ray beam by the object being imaged. Each detector element of the array produces a separate electrical signal that is a measurement of the beam intensity at the detector location. The intensity measurement from all the detectors is acquired separately to produce a transmission profile.

In some CT imaging apparatuses or systems, the x-ray source and the detector array are rotated with a gantry within the imaging plane and around the object to be imaged such that the angle at which the x-ray beam intersects the object constantly changes. A complete gantry rotation occurs when the gantry concludes one full 360-degree revolution. A group of x-ray attenuation measurements (e.g., projection data) from the detector array at one gantry angle is referred to as a view. A view is, therefore, each incremental position of the gantry. A scan of the object comprises a set of views made at different gantry angles, or view angles, during one revolution of the x-ray source and detector. Further, short scan images may also be reconstructed from a set of views acquired over less than a full gantry rotation.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called CT numbers or Hounsfield units (HU), which are used to control the brightness of a corresponding pixel on, for example, a liquid-crystal display (LCD) flat panel monitor.

FIG. 1 illustrates one example of an imaging apparatus or system 100. The imaging apparatus or system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 (also referred to herein as x-rays) for use in imaging the patient. The radiation source 104 projects x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels to increase the scanned volume size, or to scan a volume more quickly.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
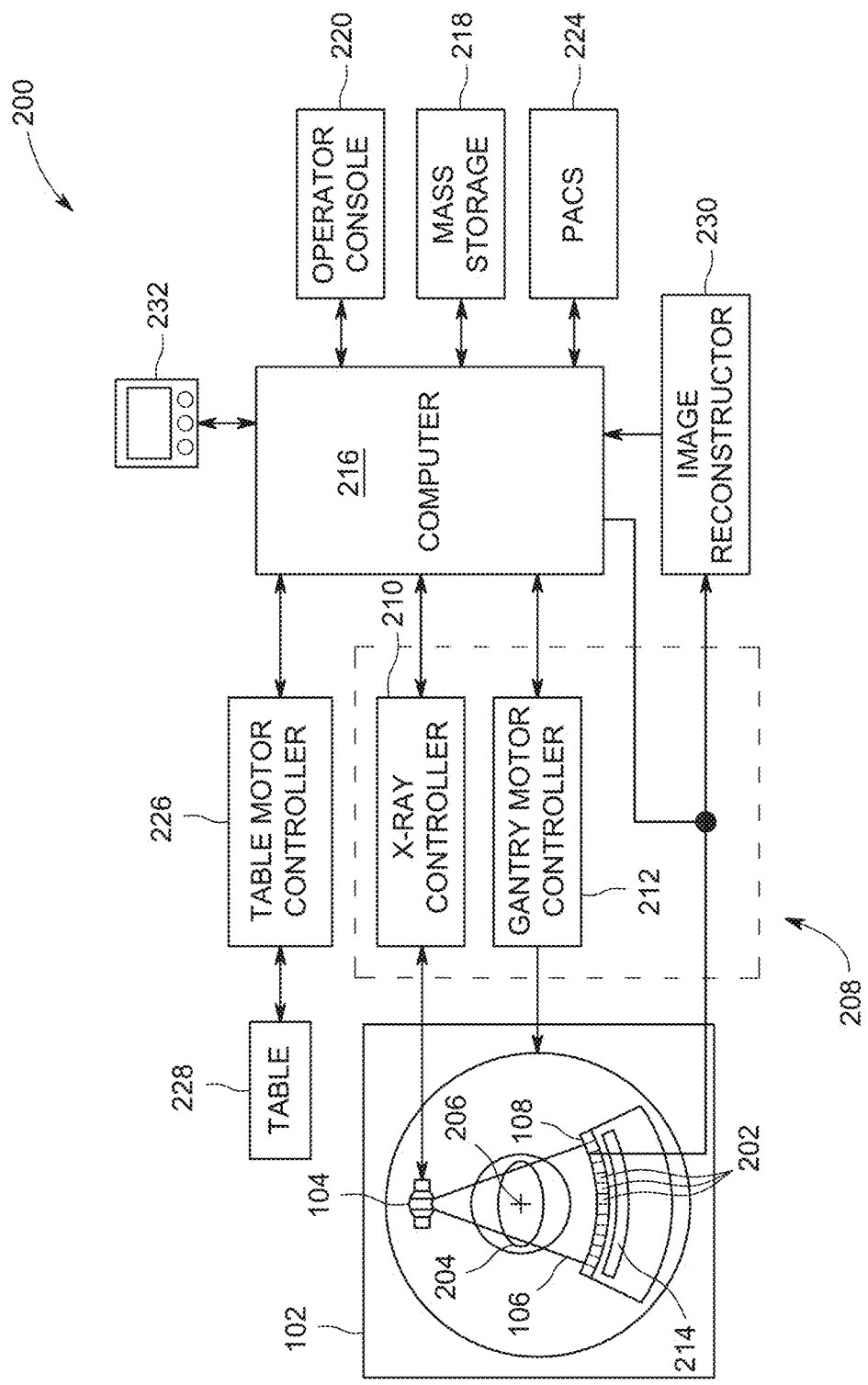
FIG. 2 illustrates a schematic diagram of the imaging system shown in FIG. 1.

FIG. 2 illustrates a schematic diagram of the imaging apparatus or system 100 shown in FIG. 1. The imaging system 100 can reconstruct images with a temporal window in real-time. In one embodiment, the system 100 includes the detector array 108 that includes a plurality of detector elements 202 that together sense the x-ray beams 106 that pass through a subject 204 (such as a patient-under-examination) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along an arc of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In one example implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 to appropriately position the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 reconstructs the images stored in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in system 200. In one embodiment, image reconstructor 230 may include such instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

Figure 3:
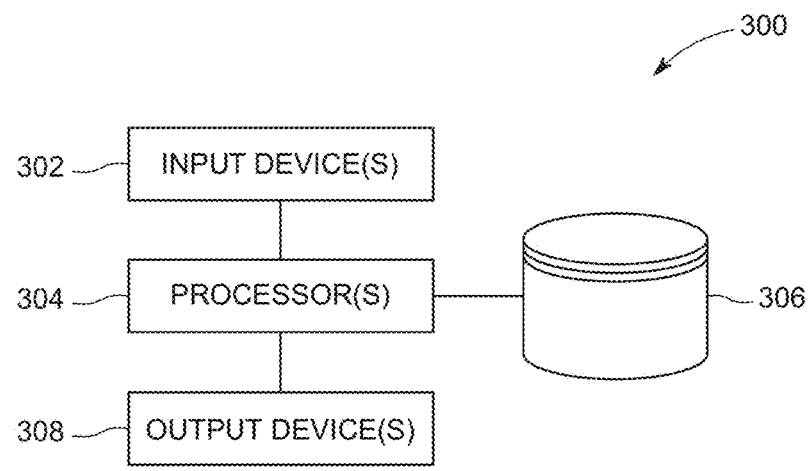
FIG. 3 schematically illustrates one embodiment of a modeling system.
Figure 4:
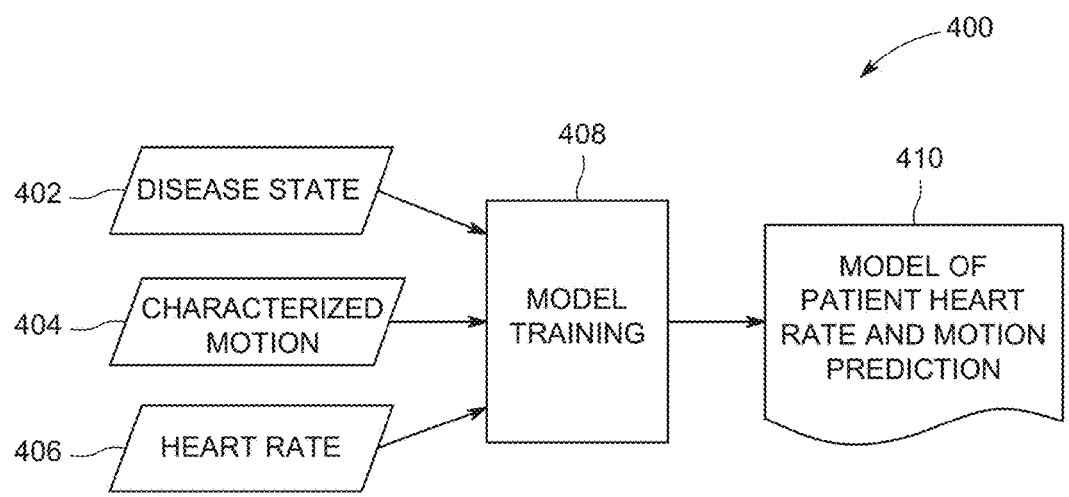
FIG. 4 illustrates a flowchart of one embodiment of a method for creating the database of historical patient data.

FIG. 3 schematically illustrates one embodiment of a modeling system 300. The modeling system 300 is used to generate the database of historical patient data described above. With continuing reference to the modeling system 300 shown in FIG. 3, FIG. 4 illustrates a flowchart of one embodiment of a method 400 for creating the database of historical patient data.

The modeling system 300 can form an integral part of the computing device 216 shown in FIG. 2, or may at least partially be a stand-alone machine that communicates with the computing device 216 (e.g., via one or more computerized communication networks, such as a local area network, wide area network, and/or the Internet). The modeling system 300 includes one or more input devices 302, such as keyboards, an electronic mouse, a touchscreen, a connector, a modem, or the like.

The input device 302 receives input historical patient data, such as cardiac disease states 402, characterized cardiac motions 404, and heart rates 406 (all shown in FIG. 4) from one or more sources, such as a computer memory, user input, or the like. The cardiac disease states 402, characterized motions 404, and heart rates 406 can correspond with each other for each set or datum of historical patient data. For example, historical patient data can be provided to the input device 302 from a memory that stores the cardiac disease of a first patient (e.g., 402), the amount and/or velocity of movement of imaged cardiac anatomy of the same first patient during one or more portions of the cardiac cycle (e.g., 404), and/or the measured heart rate of the same first patient (e.g., 406). The disease state (402) may include information about myocardial function, valvular disease, ejection fraction, stroke volume, maximum and minimum volumes of cardiac chambers, and may further include information about the cardiac rhythm, such as normal sinus rhythm, left bundle branch block, bigeminy, atrial fibrillation, or other rhythm states. The heart rate (406) may be a single value, or may be a representative set of heart rates across multiple cardiac cycles, or may be one or more summary statistics about the patient's heart rate, such as the minimum heart rate, maximum heart rate, or the difference between an actual heart rate and the heart rate that is predicted based on the heart rate of prior beats. This historical patient data of the first patient can be associated with each other and/or an identifier of the first patient. This historical patient data also can be obtained for one or more second (and additional) patients. The historical patient data can be received for a variety of different disease states 402, characterized motions 404, and heart rates 406.

Figure 5:
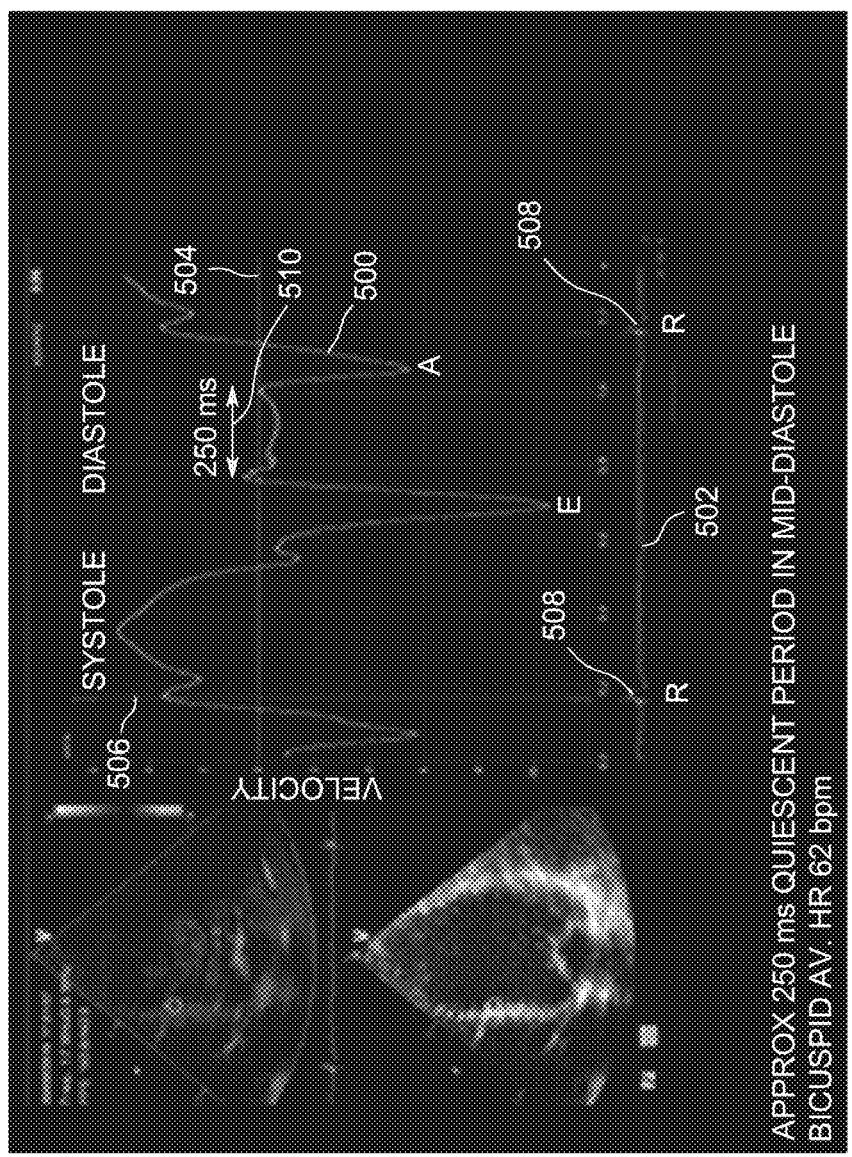
FIG. 5 illustrates cardiac velocity and a corresponding electrocardiogram for a first patient.
Figure 6:
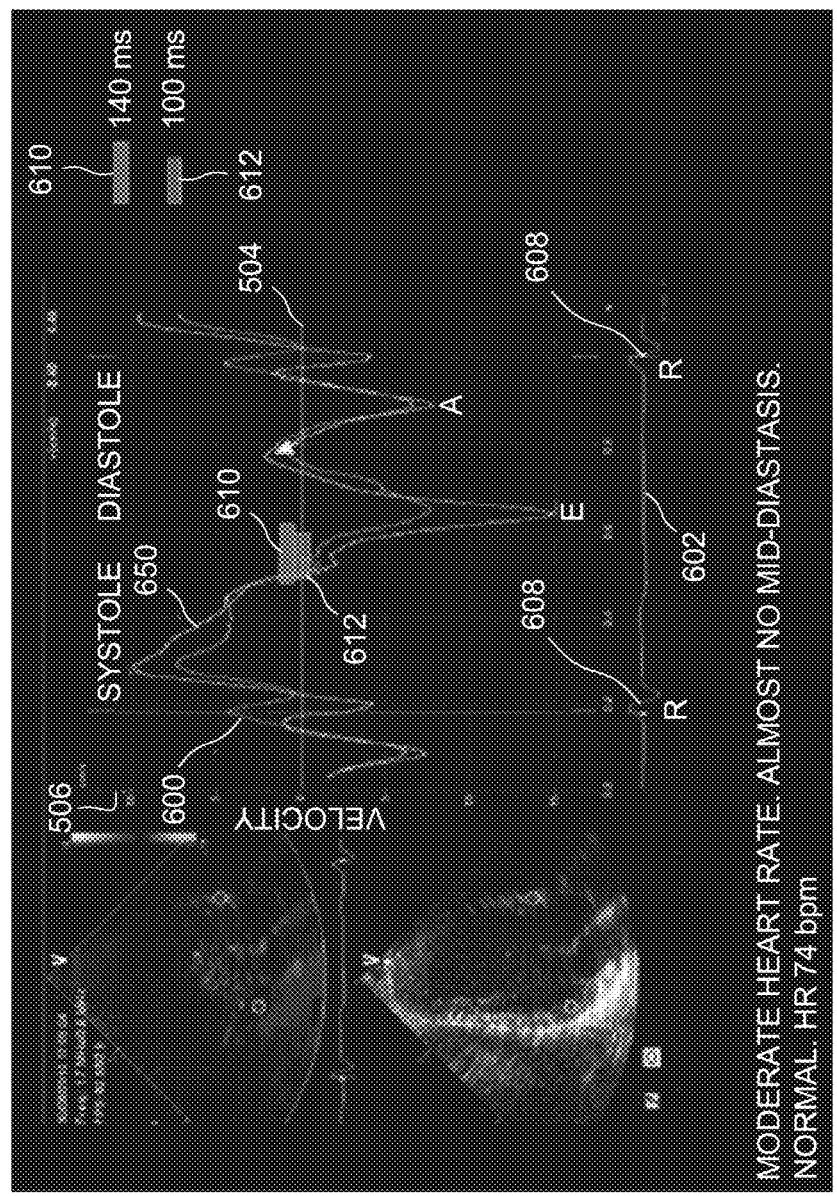
FIG. 6 illustrates cardiac velocity and a corresponding electrocardiogram for a second patient.

With respect to the characterized motions 404 that are received for plural different patients, FIGS. 5 and 6 illustrate cardiac velocities 500, 600, 650 and corresponding electrocardiograms 502, 602 for two different patients. The cardiac velocities 500, 600, 650 are shown alongside a horizontal axis 504 representative of time and a vertical axis 506 representative of how quickly a target cardiac anatomy of the heart is moving (e.g., toward and away from a reference point). FIG. 6 shows two cardiac velocities 600, 650, each representing the movement of a different target cardiac anatomy of the same patient. The electrocardiograms 502, 602 are shown alongside the horizontal axis 504, and include R-waves 508, 608 indicative of heart rates of the patients.

A time duration 510 in FIG. 5 represents a portion of the cardiac cycle with very little cardiac motion, which lasts approximately 250 milliseconds in the illustrated example. In FIG. 6, time bars 610, 612 represent durations of 140 milliseconds and 100 milliseconds, respectively, during which there is very little cardiac motion. The time durations or bars 610, 612 can be useful to compare with the velocity curves 600, 650 due to the cardiac motion in the time windows (represented by the bars 610, 612) potentially leading to motion-related artifacts within resultant generated images.

Cardiac motions of the patients associated with the cardiac velocities 500, 600, 650 and corresponding electrocardiograms 502, 602 can be portions of an R-R interval (e.g., the time from one R-wave 508, 608 to the next subsequent R-wave 508, 608), such as percentages, fractions, or the like, of the R-R interval. This portion of the R-R interval can be the time during which the target cardiac anatomy has little to no velocity. In the example shown in FIG. 5, the characterized motion 404 of the first patient can be a 250-millisecond time occurring during the middle of diastole. This characterized motion 404 can occur around or within 70 to 90% of the R-R interval shown in FIG. 5. In the example shown in FIG. 6, the characterized motion 404 of one target cardiac anatomy of the second patient can be a 100-millisecond time in the velocity 600 and occurring between systole and diastole, while the characterized motion 404 of another target cardiac anatomy of the second patient can be a 140-millisecond time in the velocity 650 and occurring between systole and diastole. These characterized motions 404 can occur around or within 40-60% of the R-R interval shown in FIG. 6.

Returning to the description of the system 300 and the method 400 shown in FIGS. 3 and 4, the input device 302 can receive the cardiac disease states 402, characterized cardiac motions 404, and heart rates 406 associated with different patients and communicate this data to one or more processors 304 of the system 300. The one or more processors 304 represent hardware circuitry that includes and/or is connected with one or more microprocessors, field programmable gate arrays, and/or integrated circuits. The one or more processors 304 are referred to in the singular here to represent the operations that are performed by a single processor 304, that are shared among multiple processors 304, or that are each performed by a different one of plural processors 304. The processor(s) 304 can be specially programmed to perform the operations described herein.

The processor 304 receives the patient historical data for many different patients (e.g., from the PACS 224 and/or another source) and creates (at model training 408) a database model 410 of this patient historical data. The model 410 can be created by the processor 304 associating different patients having the same or similar cardiac disease states 402, the same or similar characterized motions 404, and the same or similar heart rates 406 with each other. For example, the processor 304 can group portions of the patient historical data with each other for those portions that are statistically similar. The model 410 that is output can then be used to predict the characterized motion 404 for a patient having a cardiac disease state 402 and/or heart rate 406 that is identical or similar to one or more portions of the patient historical data. In one embodiment, the model 410 is saved or otherwise recorded in a storage device 306, which may be a database or other memory structure (e.g., the same storage device 218 or another storage device 218).

Figure 7:
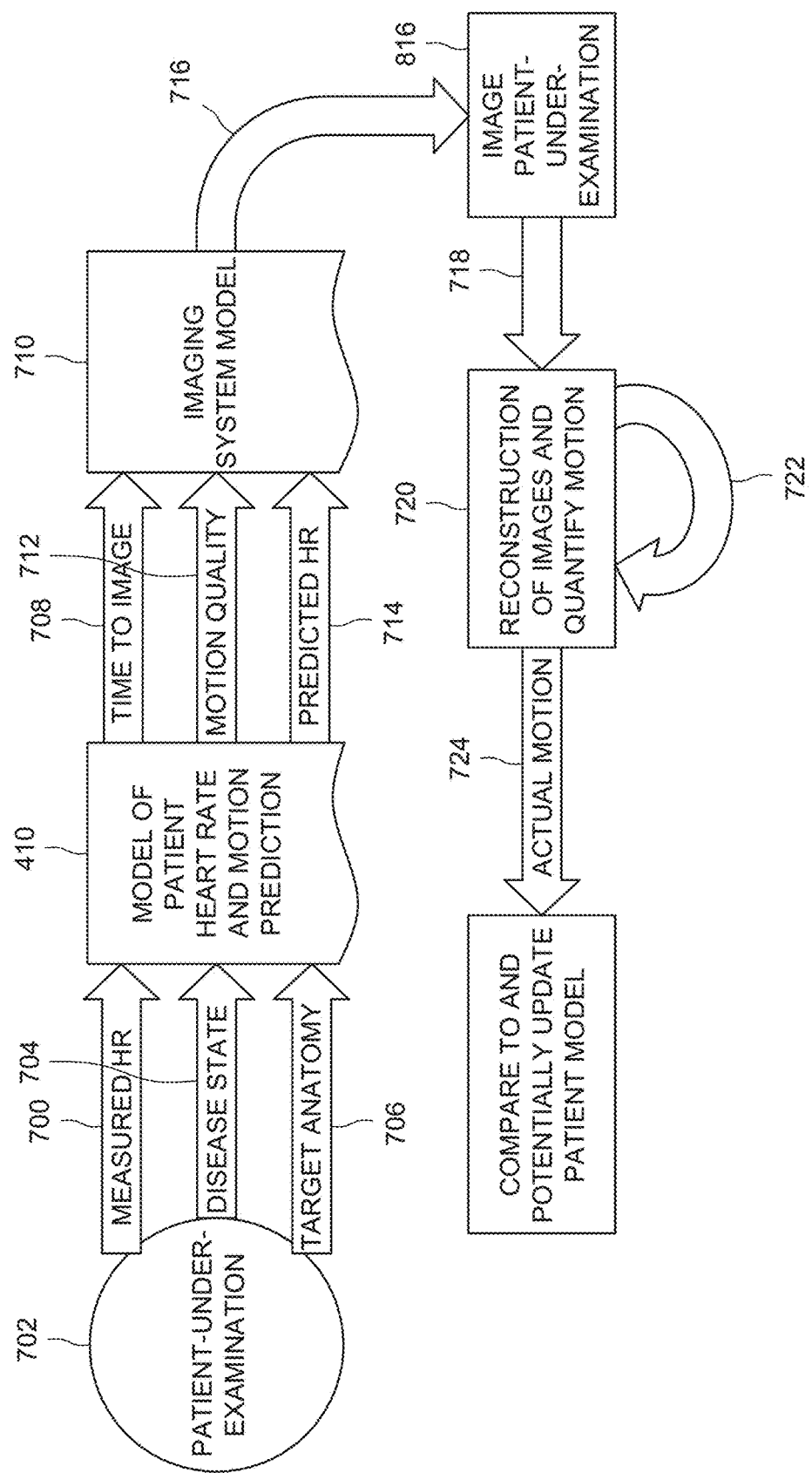
FIG. 7 illustrates a data flow diagram illustrating one embodiment of operation of a computing device shown in FIG. 2 to learn the data acquisition phase for a patient-under-examination based on the model of historical patient data, and optionally to image the patient-under-examination and modify the model.
Figure 8:
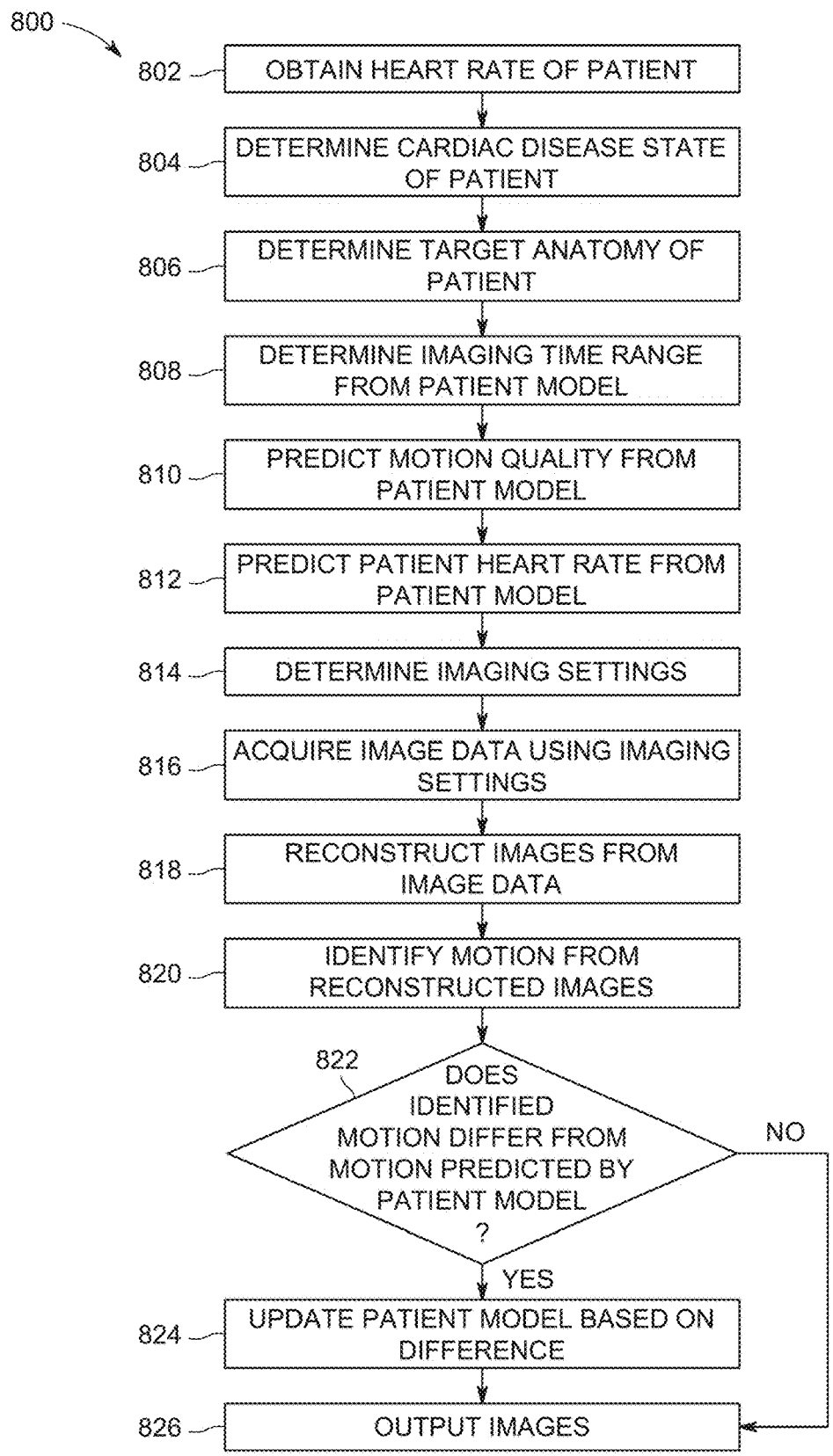
FIG. 8 illustrates a corresponding flowchart of one embodiment of a method for learning the data acquisition phase and optionally modifying the model of historical patient data.

FIG. 7 illustrates a data flow diagram illustrating one embodiment of operation of the computing device 216 shown in FIG. 2 to learn the data acquisition phase for a patient-under-examination based on the model of historical patient data, and optionally to image the patient-under-examination and modify the model. FIG. 8 illustrates a corresponding flowchart of one embodiment of a method 800 for learning the data acquisition phase and optionally modifying the model of historical patient data. The method 800 can represent the operations performed in connection with the data flows illustrated in FIG. 7. In one embodiment, the method 800 represents at least some operations performed by the computing device 216 and optionally by the processor 304 of the modeling system 300.

At 802, the heart rate 700 of the patient-under-examination 702 is obtained. The heart rate 700 may be for a single beat, or for multiple beats. It may be obtained during normal breathing, or during a specific breath hold state, such as during a prolonged breath hold of, for example, 10 to 15 seconds. In many patients, the heart rate lowers and stabilizes during a breath hold. This heart rate 700 can be measured prior to imaging of the patient's 702 target cardiac anatomy. For example, an operator of the imaging apparatus or system 100 can measure the heart rate 700 of the patient 702. At 804, a cardiac disease state 704 of the patient 702 is determined. This cardiac disease state 704 can be reported or input by the patient 702 and/or the operator of the imaging system 100, or may be obtained from an electronic medical record of the patient 702. The cardiac disease state 704 can indicate the presence (or absence) of cardiac disease, the identity or type of cardiac disease, and/or the severity of the cardiac disease.

At 806, a target cardiac anatomy 706 of the patient 702 is determined. The target cardiac anatomy 706 can identify a portion of the heart of the patient 702 that is to be imaged. For example, the target cardiac anatomy 706 can include coronary arteries, a valve, ventricle, atrium, or the like, for imaging. The target cardiac anatomy 706 can be input into the computing device 216 by an operator of the imaging system 100 or can be obtained from an electronic order for the images of the patient 702.

These parameters of the patient 702 (e.g., the heart rate 700, the cardiac disease state 704, and/or the target cardiac anatomy 706) can then be input into the model 410 created from the patient historical data. For example, the computing device 216 can examine the model 410 to determine which patients or sets of patients represented by data forming the model 410 have heart rates that are similar (e.g., within the designated range) or identical to the heart rate 700 of the patient 702, have the same cardiac disease states as the cardiac disease state 704 of the patient 702, and/or have the same target cardiac anatomy as the target cardiac anatomy 706 of the patient 702. Optionally, the computing device 216 can examine the model 410 to identify one or more patients having heart rates, cardiac disease states, and/or target cardiac anatomies that have differences from the heart rate 700, cardiac disease state 704, and/or target cardiac anatomy 706 of the patient 702 that are not statistically significant.

At 808, an image acquisition time range for the patient-under-examination is determined. The computing device 216 can examine the model 410 and identify one or more image acquisition time ranges 708 ("Time To Image" in FIG. 7) over which the target cardiac anatomy 706 of the patient 702 should be imaged. For example, the model 410 may reveal the portions of the R-R interval of the patient 702 over which the target cardiac anatomy 706 should be exposed to x-rays based on when there is little to no identified motion in the same target cardiac anatomy of other patients having the same cardiac disease state and/or having the same or similar heart rate as the patient-under-examination 702. Different heart rates, different target cardiac anatomies, and/or different cardiac disease states can result in the image acquisition time range being different.

In order to reconstruct a cardiac CT image, data must be acquired for some minimum fraction of a rotation of the CT gantry 102, such as 240 degrees or 360 degrees. When data is acquired over a longer interval, portions of that data can be used to reconstruct images at different times. Typically, the time corresponding to the center of the data window, expressed as a percentage of the R-to-R interval, is used to describe the "phase" or time of the corresponding image. Other references can be used, such as the phase or time of the beginning of the data window or the end of the data window. The image acquisition time range 708 that is determined can be an interval described by a fraction or percentage of the R-R interval of the patient 702, such as 70% (e.g., acquisition of a minimum data acquisition window is centered on the point in time that is 70% of an R-to-R interval after an R-wave), 40-80%, or the like. Alternatively, the image acquisition time range 708 can be represented in another way.

Optionally, more than one image acquisition time range 708 can be determined from the model 410. There may be several different image acquisition time ranges 708 during which the same target cardiac anatomy of other patients having the same cardiac disease state and/or having the same or similar heart rate as the patient-under-examination 702 has reduced motion. The different image acquisition time ranges 708 can be associated with different exposure confidence metrics. The exposure confidence metrics can be calculated by the computing device 216 and/or processor 304 using the patient population model, and represent likelihoods that different image acquisition time ranges result in the image data of the target cardiac anatomy being generated with less cardiac motion (than another time range). For example, a first image acquisition time range can be associated with first confidence metric; a shorter, second image acquisition time range can be associated with second confidence metric that close to (e.g., within 3% of) the first confidence metric; and a third confidence metric can be associated with a much smaller third confidence metric. Because the third confidence metric represents a much smaller potential of obtaining images with reduced motion, the computing device 216 may not select the image acquisition time range 708 associated with the third confidence metric. The second confidence metric is slightly smaller than the first confidence metric, but has a shorter image acquisition time range (which means less exposure of the patient 702 to x-rays). Therefore, the computing device 216 can select the second image acquisition time range to have approximately the same likelihood of obtaining images with reduced motion while decreasing the exposure of the patient 702 to x-rays.

The confidence metrics can be modified, weighted, or calculated based on additional factors, such as the cardiac disease state 704 of the patient 702, the gender of the patient 702, the age of the patient 702, and/or the target cardiac anatomy 706 of the patient 702. For example, the confidence metrics can be reduced for certain types of cardiac diseases and/or progressions of cardiac diseases, for female patients 702, for younger patients 702, and/or for certain parts of the heart relative to an absence of or different cardiac disease, male patients 702, older patients, and/or other parts of the heart. The confidence metric can be reduced for these factors because patients 702 having certain cardiac disease states, that are female, that are young, and/or that are having certain parts of their heart imaged may be at greater risk for harmful side effects to surrounding tissue during imaging. The computing device 216 can select an image acquisition time range 708 from the model 410 based on the associated confidence metric.

At 810, a predicted motion quality 712 of the target cardiac anatomy 706 is determined. The predicted motion quality 712 is a quantified amount of movement that the target cardiac anatomy 706 is expected or estimated to move during the image acquisition time range 708, and may be determined by the computing device 216 from the model 410. For example, as described above, different image acquisition time ranges can be associated with different movements of the target cardiac anatomy 706 by the model 410. The predicted motion quality 712 can be quantified as the peak velocity of the target cardiac anatomy 706 during the image acquisition time range 708 in the model 410. Optionally, the predicted motion quality can be quantified as the displacement of the target cardiac anatomy 706 during the image acquisition time range 708 in the model 410 (e.g., the integral of the velocity of the target cardiac anatomy 706 during the image acquisition time range 708 in the model 410). Optionally, the predicted motion quality can be quantified in another way.

At 812, a predicted heart rate 714 of the patient 702 is determined. The predicted heart rate 714 can be the heart rate that the patient 702 is expected or estimated to have during imaging of the target cardiac anatomy 706. This predicted heart rate 714 can be obtained by the computing device 216 from the model 410. For example, the model 410 may store the heart rates of the patients (having the same cardiac disease state 704, the same target anatomy 706, and/or the same or similar pre-imaging measured heart rate 700) during imaging. The heart rates of the patients before imaging (e.g., the measured heart rate 700) may differ (e.g., be slower) than during imaging. The predicted heart rate 714 can be the heart rate that the patient 702 is predicted to have during imaging based on the heart rates that other, similar patients had during imaging.

At 814, imaging settings 716 of the imaging system 100 are determined. In one embodiment, the imaging settings 716 include the time(s) at which the imaging system 100 is to generate and transmit x-rays through the target cardiac anatomy 706 of the patient 702 and/or the angle of rotation through which the x-ray source and detector array are rotated around the target cardiac anatomy 706. Optionally, one or more other settings or configurations of the imaging system 100 may be determined. The imaging settings 716 can be determined using an imaging system model 710, which is one or more mathematical relationships between (a) the image acquisition time range 708 and/or the predicted heart rate 714 and (b) the time(s) at which the imaging system 100 is to generate and transmit x-rays through the target cardiac anatomy 706 of the patient 702 and/or the angle of rotation through which the x-ray source and detector array are rotated around the target cardiac anatomy 706. This model 710 can translate the selected image acquisition time range 708 and/or the predicted heart rate 714 into the angular rotation range and times at which x-rays are transmitted by the imaging system 100 so that the target cardiac anatomy 706 is imaged during the selected portion of the R-R interval (that corresponds with the selected image acquisition time range 708).

These imaging settings 716 can be determined by the computing device 216 from the imaging system model 710, and can be used to control the imaging system 100 to image the target cardiac anatomy 706 of the patient 702, at 816. Imaging the patient 702 generates image data 718, which is used to reconstruct one or more images (e.g., reconstructed images 720) of the target cardiac anatomy 706, at 818. The image data 718 may be iteratively reconstructed 722 for different phases of motion of the target cardiac anatomy 706.

In one embodiment, operation of the method 800 can terminate once the reconstructed image or images are obtained at 818. As described above, the images can be acquired with less motion of the target cardiac anatomy 706 and with decreased exposure of the patient 702 to x-rays relative to using a default portion of the R-R interval to image the target cardiac anatomy 706. This can provide for a safer and more accurate technique for acquiring images of the target cardiac anatomy 706.

Alternatively, the method 800 can proceed by determining, at 822, whether actual motion in the target cardiac anatomy 706 during image acquisition in the image acquisition time range 708 was the same as or similar to the predicted motion quality 712. For example, at 820, motion 724 in the target cardiac anatomy 706 can be identified from the reconstructed images 720. This motion 724 can be quantified using reconstruction techniques (such as SMART PHASE from GE Healthcare) or post-reconstruction techniques (such as SNAPSHOT FREEZE from GE Healthcare) to measure cardiac motion versus phase of the target cardiac anatomy 706. At 822, the measured motion 724 can be compared with the predicted motion 712. For example, the computing device 216 can determine if the motion of the target cardiac anatomy 706 that was predicted from the model 410 at 810 is the same or similar to the actual motion 724 of the target cardiac anatomy 706. The motions may be the same or similar if the target cardiac anatomy 706 is displaced by the same distances or by different distances that are within a designated range (e.g., within 3%, within 5%, or within 10%) and/or if the velocity of the target cardiac anatomy 706 in the actual motion 724 is the same or similar (within a designated range, such as within 3%, within 5%, or within 10%) as the predicted velocity (e.g., the predicted motion 712).

If the predicted and actual motions 712, 724 are the same or similar, then the actual motion 724 of the target cardiac anatomy 706 may not differ from the predicted motion 712. As a result, flow of the method 800 can proceed toward 826, where the reconstructed images 720 are output. The reconstructed images 720 can be output by presenting the images 720 on an electronic display, by printing the images 720, or the like.

But, if the predicted and actual motions 712, 724 are not the same or similar, then the actual motion 724 of the target cardiac anatomy 706 may differ from the predicted motion 712. As a result, the model 410 may need to be updated and flow of the method 800 can proceed toward 824. At 824, the model 410 is updated. For example, the computing device 216 can report the actual motion 724 of the target cardiac anatomy 706, as well as an identity of the target cardiac anatomy 706, the heart rate of the patient 702 during imaging, the gender of the patient 702, the age of the patient 702, the cardiac disease state of the patient 702, and/or the like, to the processor 304 of the system 300. The processor 304 can then modify the model 410 by including this information in the model 410. For example, the motion 724 of the target cardiac anatomy 706 can be used to update the model 410 to reflect that the motion 724 occurred for the patient 702 having the target cardiac anatomy 706, the cardiac disease state, 704, the heart rate 700, and so on. The model 710 is updated to more accurately reflect what motion is predicted to occur for other patients having the same or similar target cardiac anatomy 706, cardiac disease state 704, heart rate 700, and the like. Flow of the method 800 can then proceed toward 826 or may terminate.

In one embodiment, an imaging system includes one or more processors configured to determine one or more of a heart rate of a patient under examination, a cardiac disease state of the patient under examination, and/or an imaging target portion of cardiac anatomy of the patient under examination. The one or more processors also are configured to calculate an image acquisition time range from a patient population model using the one or more of the heart rate, the cardiac disease state, or the imaging target portion of the cardiac anatomy. The patient population model represents relationships between cardiac motion of plural other patients and one or more of time or cardiac phases of the other patients. The one or more processors also are configured to determine imaging configuration settings for an imaging assembly to acquire image data of the target cardiac anatomy of the patient under examination during the image acquisition time range that is calculated using the patient population model. Imaging the target cardiac anatomy of the patient under examination using the imaging assembly operating according to the imaging configuration settings generates image data of the target cardiac anatomy having less cardiac motion and/or a reduced image acquisition time range relative to determining the imaging configuration settings without using the patient population model. The one or more processors are configured to generate and communicate a control signal that directs the imaging assembly to image the target cardiac anatomy of the patient under examination using the imaging configuration settings. The one or more processors also configured to receive imaging data from the imaging assembly, to reconstruct one or more images of the target cardiac anatomy using the imaging data, and to one or more of direct display of the one or more images on an electronic display device or direct storage of the one or more images in a tangible and non-transitory computer readable storage medium.

Optionally, the one or more processors are configured to calculate one or more of an estimated motion quality of the target cardiac anatomy of the patient under examination or a predicted heart rate of the patient under examination from the patient population model and using the one or more of the heart rate, the cardiac disease state, or the imaging target portion of the cardiac anatomy. The one or more processors can be configured to determine the imaging configuration settings using the one or more of the estimated motion quality or the predicted heart rate.

Optionally, the one or more processors are configured to calculate the image acquisition time range by determining a portion of an R-R wave interval during which imaging of the target cardiac anatomy is to occur. The portion of the R-R wave interval can be different for one or more of different heart rates of the patient under examination, different cardiac disease states of the patient under examination, and/or different imaging target portions of the cardiac anatomy of the patient under examination.

Optionally, the one or more processors are configured to reconstruct the one or more images of the target cardiac anatomy for different phases of motion of the target cardiac anatomy. The one or more processors also can be configured to select at least one of the images of the target cardiac anatomy based on an amount of motion of the target cardiac anatomy during the phase of motion of the target cardiac anatomy that is associated with the at least one of the images that is selected, to compare the phase of motion of the target cardiac anatomy that is associated with the at least one of the images that is selected with the image acquisition time range that is calculated from the patient population model, and to update the patient population model based on a difference between the phase of motion of the target cardiac anatomy and the image acquisition time range that is calculated from the patient propulsion model.

Optionally, the one or more processors are configured to calculate exposure confidence metrics using the patient population model. The exposure confidence metrics can represent of likelihoods that different image acquisition time ranges calculated using the patient population model result in the image data of the target cardiac anatomy being generated with less cardiac motion. The one or more processors can be configured to determine the imaging configuration settings based on the exposure confidence metrics.

Optionally, the one or more processors are configured to calculate the exposure confidence metrics to be different for one or more of different cardiac disease states, different patient genders, different target cardiac anatomies, and/or different patient ages.

Optionally, the one or more processors are configured to reduce at least one of the exposure confidence metrics responsive to one or more of the patient exhibiting presence of a cardiac disease or the patient being female.

In one embodiment, a method includes determining one or more of a heart rate of a patient under examination, a cardiac disease state of the patient under examination, and/or an imaging target portion of cardiac anatomy of the patient under examination. The method also includes calculating an image acquisition time range from a patient population model using the one or more of the heart rate, the cardiac disease state, and/or the imaging target portion of the cardiac anatomy. The patient population model represents relationships between cardiac motion of plural other patients and one or more of time or cardiac phases of the other patients. The method also includes determining imaging configuration settings for an imaging system to acquire image data of the target cardiac anatomy of the patient under examination during the image acquisition time range that is calculated using the patient population model. Imaging the target cardiac anatomy of the patient under examination using the imaging configuration settings for the imaging system generates image data of the target cardiac anatomy having less cardiac motion and/or a reduced image acquisition time range relative to determining the imaging configuration settings without using the patient population model.

Optionally, the method also includes calculating one or more of an estimated motion quality of the target cardiac anatomy of the patient under examination or a predicted heart rate of the patient under examination from the patient population model and using the one or more of the heart rate, the cardiac disease state, or the imaging target portion of the cardiac anatomy. The imaging configuration settings also can be determined using the one or more of the estimated motion quality or the predicted heart rate.

Optionally, the method also includes imaging the target cardiac anatomy of the patient under examination using the imaging configuration settings.

Optionally, calculating the image acquisition time range includes determining a portion of an R-R wave interval during which imaging of the target cardiac anatomy is to occur. The portion of the R-R wave interval can be different for one or more of different heart rates of the patient under examination, different cardiac disease states of the patient under examination, and/or different imaging target portions of the cardiac anatomy of the patient under examination.

Optionally, the method also includes reconstructing images of the target cardiac anatomy of the patient under examination. The images can be reconstructed for different phases of motion of the target cardiac anatomy. The method also can include selecting at least one of the images of the target cardiac anatomy based on an amount of motion of the target cardiac anatomy during the phase of motion of the target cardiac anatomy that is associated with the at least one of the images that is selected, comparing the phase of motion of the target cardiac anatomy that is associated with the at least one of the images that is selected with the image acquisition time range that is calculated from the patient population model, and updating the patient population model based on a difference between the phase of motion of the target cardiac anatomy and the image acquisition time range that is calculated from the patient propulsion model.

Optionally, the method also includes calculating exposure confidence metrics using the patient population model. The exposure confidence metrics can represent likelihoods that different image acquisition time ranges calculated using the patient population model result in the image data of the target cardiac anatomy being generated with less cardiac motion. The imaging configuration settings can be determined based on the exposure confidence metrics.

Optionally, the exposure confidence metrics are calculated to be different for one or more of different cardiac disease states, different patient genders, and/or different target cardiac anatomies.

In one embodiment, a tangible and non-transitory computer readable storage medium including instructions is provided. The instructions direct one or more processors to determine one or more of a heart rate of a patient under examination, a cardiac disease state of the patient under examination, and/or an imaging target portion of cardiac anatomy of the patient under examination and to calculate an image acquisition time range from a patient population model using the one or more of the heart rate, the cardiac disease state, and/or the imaging target portion of the cardiac anatomy. The patient population model represents relationships between cardiac motion of plural other patients and one or more of time or cardiac phases of the other patients. The instructions also direct the one or more processors to determine imaging configuration settings for an imaging system to acquire image data of the target cardiac anatomy of the patient under examination during the image acquisition time range that is calculated using the patient population model. Imaging the target cardiac anatomy of the patient under examination using the imaging configuration settings for the imaging system generates image data of the target cardiac anatomy having less cardiac motion and/or a reduced image acquisition time range relative to determining the imaging configuration settings without using the patient population model.

Optionally, the instructions also direct the one or more processors to calculate one or more of an estimated motion quality of the target cardiac anatomy of the patient under examination or a predicted heart rate of the patient under examination from the patient population model and using the one or more of the heart rate, the cardiac disease state, and/or the imaging target portion of the cardiac anatomy. The imaging configuration settings also can be determined using the one or more of the estimated motion quality or the predicted heart rate.

Optionally, the instructions also direct the one or more processors to direct imaging the target cardiac anatomy of the patient under examination using the imaging configuration settings.

Optionally, the instructions also direct the one or more processors to calculate the image acquisition time range by determining a portion of an R-R wave interval during which imaging of the target cardiac anatomy is to occur. The portion of the R-R wave interval can be different for one or more of different heart rates of the patient under examination, different cardiac disease states of the patient under examination, and/or different imaging target portions of the cardiac anatomy of the patient under examination.

Optionally, the instructions also direct the one or more processors to reconstruct images of the target cardiac anatomy of the patient under examination. The images can be reconstructed for different phases of motion of the target cardiac anatomy. The instructions also can direct the one or more processors to select at least one of the images of the target cardiac anatomy based on an amount of motion of the target cardiac anatomy during the phase of motion of the target cardiac anatomy that is associated with the at least one of the images that is selected, to compare the phase of motion of the target cardiac anatomy that is associated with the at least one of the images that is selected with the image acquisition time range that is calculated from the patient population model, and to update the patient population model based on a difference between the phase of motion of the target cardiac anatomy and the image acquisition time range that is calculated from the patient propulsion model.

Optionally, the instructions also direct the one or more processors to calculate exposure confidence metrics using the patient population model. The exposure confidence metrics can represent likelihoods that different image acquisition time ranges calculated using the patient population model result in the image data of the target cardiac anatomy being generated with less cardiac motion. The imaging configuration settings can be determined based on the exposure confidence metrics.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system comprising:
one or more processors configured to determine one or more of a heart rate of a patient under examination, a cardiac disease state of the patient under examination, or an imaging target portion of cardiac anatomy of the patient under examination, the one or more processors also configured to calculate an image acquisition time range from a patient population model using the one or more of the heart rate, the cardiac disease state, or the imaging target portion of the cardiac anatomy,
wherein the patient population model representing relationships between cardiac motion of plural other patients and one or more of time or cardiac phases of the other patients,
wherein the one or more processors also are configured to determine imaging configuration settings for an imaging assembly to acquire image data of the target cardiac anatomy of the patient under examination during the image acquisition time range that is calculated using the patient population model,
wherein imaging the target cardiac anatomy of the patient under examination using the imaging assembly operating according to the imaging configuration settings one or more of:
generates image data of the target cardiac anatomy having less cardiac motion than determining the imaging configuration settings without using the patient population model or
acquires the image data during an image acquisition time range that is reduced relative to determining the imaging configuration settings without using the patient population model,
wherein the one or more processors are configured to generate and communicate a control signal that directs the imaging assembly to image the target cardiac anatomy of the patient under examination using the imaging configuration settings, the one or more processors also configured to receive imaging data from the imaging assembly, to reconstruct one or more images of the target cardiac anatomy using the imaging data, and to one or more of direct display of the one or more images on an electronic display device or direct storage of the one or more images in a tangible and non-transitory computer readable storage medium.

2. The system of claim 1, wherein the one or more processors are configured to calculate one or more of an estimated motion quality of the target cardiac anatomy of the patient under examination or a predicted heart rate of the patient under examination from the patient population model and using the one or more of the heart rate, the cardiac disease state, or the imaging target portion of the cardiac anatomy,
wherein the one or more processors are configured to determine the imaging configuration settings using the one or more of the estimated motion quality or the predicted heart rate.

3. The system of claim 1, wherein the one or more processors are configured to calculate the image acquisition time range by determining a portion of an R-R wave interval during which imaging of the target cardiac anatomy is to occur, wherein the portion of the R-R wave interval is different for one or more of different heart rates of the patient under examination, different cardiac disease states of the patient under examination, or different imaging target portions of the cardiac anatomy of the patient under examination.

4. The system of claim 1, wherein the one or more processors are configured to reconstruct the one or more images of the target cardiac anatomy for different phases of motion of the target cardiac anatomy,
wherein the one or more processors also are configured to select at least one of the images of the target cardiac anatomy based on an amount of motion of the target cardiac anatomy during the phase of motion of the target cardiac anatomy that is associated with the at least one of the images that is selected, to compare the phase of motion of the target cardiac anatomy that is associated with the at least one of the images that is selected with the image acquisition time range that is calculated from the patient population model, and to update the patient population model based on a difference between the phase of motion of the target cardiac anatomy and the image acquisition time range that is calculated from the patient propulsion model.

5. The system of claim 1, wherein the one or more processors are configured to calculate exposure confidence metrics using the patient population model,
wherein the exposure confidence metrics represent of likelihoods that different image acquisition time ranges calculated using the patient population model result in the image data of the target cardiac anatomy being generated with less cardiac motion,
wherein the one or more processors are configured to determine the imaging configuration settings based on the exposure confidence metrics.

6. The system of claim 5, wherein the one or more processors are configured to calculate the exposure confidence metrics to be different for one or more of different cardiac disease states, different patient genders, different target cardiac anatomies, or different patient ages.

7. The system of claim 5, wherein the one or more processors are configured to reduce at least one of the exposure confidence metrics responsive to one or more of the patient exhibiting presence of a cardiac disease or the patient being female.

8. A method comprising:
determining one or more of a heart rate of a patient under examination, a cardiac disease state of the patient under examination, or an imaging target portion of cardiac anatomy of the patient under examination;
calculating an image acquisition time range from a patient population model using the one or more of the heart rate, the cardiac disease state, or the imaging target portion of the cardiac anatomy, the patient population model representing relationships between cardiac motion of plural other patients and one or more of time or cardiac phases of the other patients; and
determining imaging configuration settings for an imaging system to acquire image data of the target cardiac anatomy of the patient under examination during the image acquisition time range that is calculated using the patient population model,
wherein imaging the target cardiac anatomy of the patient under examination using the imaging configuration settings for the imaging system one or more of:
generates image data of the target cardiac anatomy having less cardiac motion relative to determining the imaging configuration settings without using the patient population model or
acquires the image data during a reduced image acquisition time range relative to determining the imaging configuration settings without using the patient population model.

9. The method of claim 8, further comprising:
calculating one or more of an estimated motion quality of the target cardiac anatomy of the patient under examination or a predicted heart rate of the patient under examination from the patient population model and using the one or more of the heart rate, the cardiac disease state, or the imaging target portion of the cardiac anatomy,
wherein the imaging configuration settings also are determined using the one or more of the estimated motion quality or the predicted heart rate.

10. The method of claim 8, further comprising imaging the target cardiac anatomy of the patient under examination using the imaging configuration settings.

11. The method of claim 8, wherein calculating the image acquisition time range includes determining a portion of an R-R wave interval during which imaging of the target cardiac anatomy is to occur, the portion of the R-R wave interval being different for one or more of different heart rates of the patient under examination, different cardiac disease states of the patient under examination, or different imaging target portions of the cardiac anatomy of the patient under examination.

12. The method of claim 8, further comprising:
reconstructing images of the target cardiac anatomy of the patient under examination, the images reconstructed for different phases of motion of the target cardiac anatomy;
selecting at least one of the images of the target cardiac anatomy based on an amount of motion of the target cardiac anatomy during the phase of motion of the target cardiac anatomy that is associated with the at least one of the images that is selected;
comparing the phase of motion of the target cardiac anatomy that is associated with the at least one of the images that is selected with the image acquisition time range that is calculated from the patient population model; and
updating the patient population model based on a difference between the phase of motion of the target cardiac anatomy and the image acquisition time range that is calculated from the patient propulsion model.

13. The method of claim 8, further comprising:
calculating exposure confidence metrics using the patient population model, the exposure confidence metrics representative of likelihoods that different image acquisition time ranges calculated using the patient population model result in the image data of the target cardiac anatomy being generated with less cardiac motion,
wherein the imaging configuration settings are determined based on the exposure confidence metrics.

14. The method of claim 13, wherein the exposure confidence metrics are calculated to be different for one or more of different cardiac disease states, different patient genders, or different target cardiac anatomies.

15. A tangible and non-transitory computer readable storage medium including instructions that direct one or more processors to:
determine one or more of a heart rate of a patient under examination, a cardiac disease state of the patient under examination, or an imaging target portion of cardiac anatomy of the patient under examination;
calculate an image acquisition time range from a patient population model using the one or more of the heart rate, the cardiac disease state, or the imaging target portion of the cardiac anatomy, the patient population model representing relationships between cardiac motion of plural other patients and one or more of time or cardiac phases of the other patients; and
determine imaging configuration settings for an imaging system to acquire image data of the target cardiac anatomy of the patient under examination during the image acquisition time range that is calculated using the patient population model,
wherein imaging the target cardiac anatomy of the patient under examination using the imaging configuration settings for the imaging system one or more of:
generates image data of the target cardiac anatomy having less cardiac motion relative to determining the imaging configuration settings without using the patient population model or
acquires the image data over a reduced image acquisition time range relative to determining the imaging configuration settings without using the patient population model.

16. The tangible and non-transitory computer readable storage medium of claim 15, wherein the instructions also direct the one or more processors to:
calculate one or more of an estimated motion quality of the target cardiac anatomy of the patient under examination or a predicted heart rate of the patient under examination from the patient population model and using the one or more of the heart rate, the cardiac disease state, or the imaging target portion of the cardiac anatomy,
wherein the imaging configuration settings also are determined using the one or more of the estimated motion quality or the predicted heart rate.

17. The tangible and non-transitory computer readable storage medium of claim 15, wherein the instructions also direct the one or more processors to direct imaging the target cardiac anatomy of the patient under examination using the imaging configuration settings.

18. The tangible and non-transitory computer readable storage medium of claim 15, wherein the instructions also direct the one or more processors to calculate the image acquisition time range by determining a portion of an R-R wave interval during which imaging of the target cardiac anatomy is to occur, the portion of the R-R wave interval being different for one or more of different heart rates of the patient under examination, different cardiac disease states of the patient under examination, or different imaging target portions of the cardiac anatomy of the patient under examination.

19. The tangible and non-transitory computer readable storage medium of claim 15, wherein the instructions also direct the one or more processors to:

reconstruct images of the target cardiac anatomy of the patient under examination, the images reconstructed for different phases of motion of the target cardiac anatomy;

select at least one of the images of the target cardiac anatomy based on an amount of motion of the target cardiac anatomy during the phase of motion of the target cardiac anatomy that is associated with the at least one of the images that is selected;

compare the phase of motion of the target cardiac anatomy that is associated with the at least one of the images that is selected with the image acquisition time range that is calculated from the patient population model; and update the patient population model based on a difference between the phase of motion of the target cardiac anatomy and the image acquisition time range that is calculated from the patient propulsion model.

20. The tangible and non-transitory computer readable storage medium of claim 15, wherein the instructions also direct the one or more processors to:

calculate exposure confidence metrics using the patient population model, the exposure confidence metrics representative of likelihoods that different image acquisition time ranges calculated using the patient population model result in the image data of the target cardiac anatomy being generated with less cardiac motion, wherein the imaging configuration settings are determined based on the exposure confidence metrics.

* * * * *